United States Patent
Logan et al.

(10) Patent No.: US 7,974,803 B2
(45) Date of Patent: Jul. 5, 2011

(54) METHOD AND APPARATUS FOR CALIBRATING WOOD TESTING MACHINE

(75) Inventors: James D. Logan, Pullman, WA (US); James R Allen, Pullman, WA (US); Tony L. Lee, Pullman, WA (US)

(73) Assignee: Metriguard Inc, Pullman, WA (US)

( * ) Notice: Subject to any disclaimer, the term of this patent is extended or adjusted under 35 U.S.C. 154(b) by 214 days.

(21) Appl. No.: 12/386,867

(22) Filed: Apr. 24, 2009

(65) Prior Publication Data

US 2010/0036633 A1 Feb. 11, 2010

Related U.S. Application Data

(60) Provisional application No. 61/126,153, filed on Apr. 29, 2008.

(51) Int. Cl.
*G01D 21/00* (2006.01)
(52) U.S. Cl. ............ 702/88; 702/98; 702/104; 702/105; 73/1.08; 73/1.14; 73/1.15
(58) Field of Classification Search .................... 702/88; 73/1.14, 1.15, 1.08
See application file for complete search history.

(56) References Cited

U.S. PATENT DOCUMENTS

| | | | | |
|---|---|---|---|---|
| 3,196,672 A * | 7/1965 | Keller | .............................. | 73/812 |
| 3,760,636 A * | 9/1973 | Serry | .............................. | 73/852 |
| 4,289,037 A * | 9/1981 | Vinopal | .......................... | 73/808 |
| 4,926,350 A * | 5/1990 | Bechtel et al. | .................. | 702/36 |
| 4,991,446 A * | 2/1991 | Bechtel | .......................... | 73/849 |
| 5,056,370 A * | 10/1991 | Maier | .............................. | 73/794 |
| 5,503,024 A * | 4/1996 | Bechtel et al. | .................. | 73/852 |
| 6,053,052 A * | 4/2000 | Starostovic | ...................... | 73/851 |
| 6,055,867 A * | 5/2000 | Dunne et al. | ..................... | 73/849 |
| 6,381,546 B1 * | 4/2002 | Starostovic | ...................... | 702/36 |
| 6,505,129 B2 * | 1/2003 | Starostovic et al. | ............ | 702/36 |
| 7,043,990 B2 * | 5/2006 | Wang et al. | ...................... | 73/597 |
| 7,047,156 B1 * | 5/2006 | Bechtel et al. | ................. | 702/179 |
| 7,194,916 B2 * | 3/2007 | Ouellet et al. | ................... | 73/852 |

* cited by examiner

*Primary Examiner* — Drew A Dunn
*Assistant Examiner* — Timothy Hwang

(57) ABSTRACT

This improved method of calibrating wood testing machines includes improved test bars, shim and software to direct the operator through the steps of calibration, storing interim results and calculating new calibration factors based on values read when the test bars are placed in the wood testing machine. This method avoids a number of problems in previous methods and apparatus. It properly corrects for changes in deflection in the measurement apparatus and changes in straightness of the test bars. The result is a more stable and reliable calibration that is referenced to precise measurement of the EI product for the test bar.

20 Claims, 6 Drawing Sheets

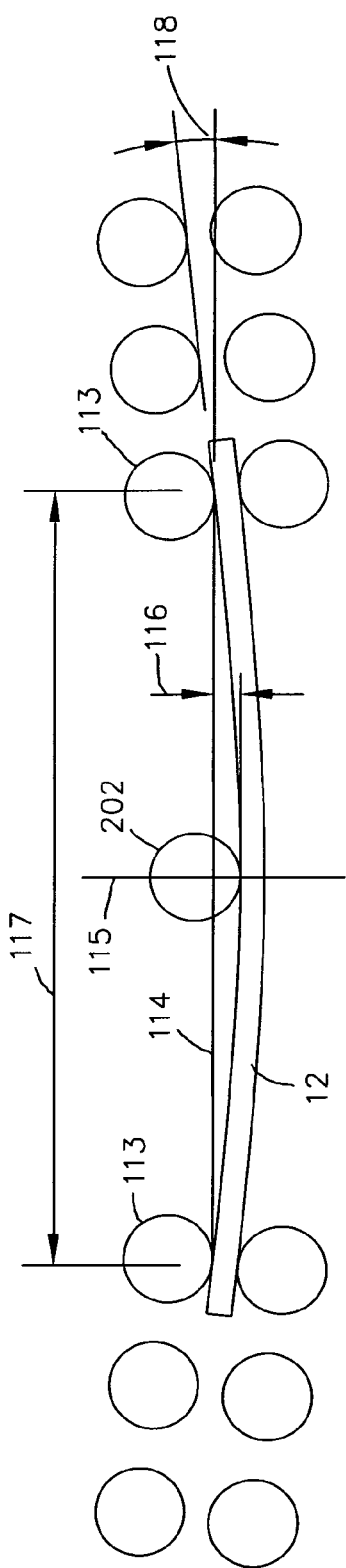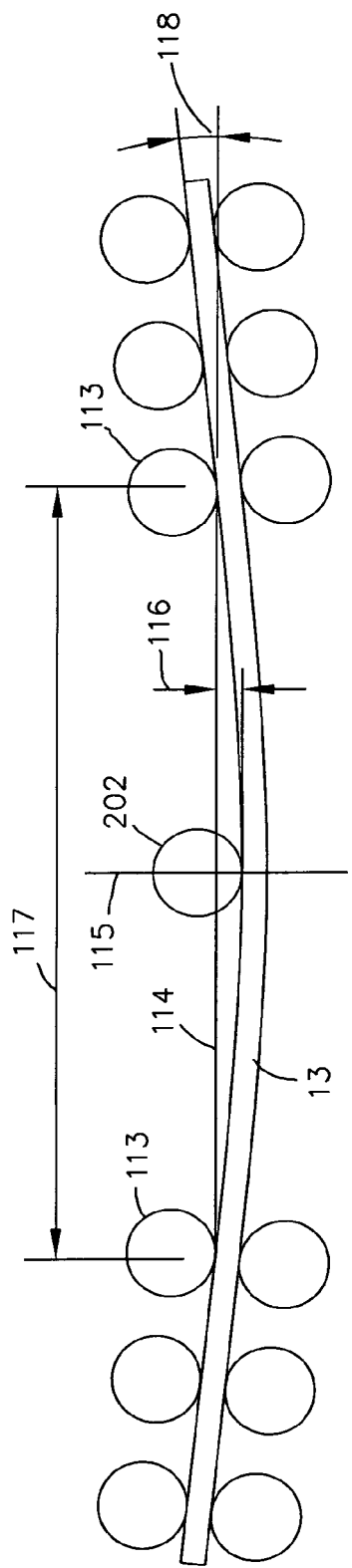

METHOD AND APPARATUS FOR CALIBRATING WOOD TESTING MACHINE

REFERENCES

1. U.S. Pat. No. 3,196,672 July 1965 Keller
2. U.S. Pat. No. 5,503,024 Apr. 2, 1996 Bechtel et al.
3. Service bulletin 850-0025 "New Calibration Process Available", Metriguard Inc., 1 Aug. 2007
4. "Model 7200 HCLT Maintenance & Operation Manual", 7200M21.W60, Metriguard Inc., 29 Apr. 1997

TECHNICAL FIELD

This invention relates to the field of structural lumber grading, and more specifically calibration of the equipment used for production of machine stress rated lumber grades.

BACKGROUND OF THE INVENTION

Lumber grading in the United States is regulated under policies of the American Lumber Standards Committee (ALSC) and the various grading agencies authorized by the ALSC. Other countries have similar arrangements for regulating the grading of structural lumber materials. Whenever materials are used in construction the reliability and serviceability of the construction relate to the safety of the people and property involved in the use of the structure so it is very important that the grading and sorting process for these materials be carried out in the most accurate way possible consistent with the needs in assessing the structural properties of the materials being tested. The present invention provides improvements in this process that result in more accurate and reliable lumber grading.

The originator of this type of equipment was Keller U.S. Pat. No. 3,196,672. The apparatus invented by Keller is still in use in many lumber production plants throughout the world, and is the inspiration behind an improved apparatus by Bechtel et al U.S. Pat. No. 5,503,024. Even though the Keller apparatus is no longer manufactured it is still maintained and is in wide use some 45 years after it was first introduced. The two machines have similar basic mechanical features; both measure the modulus of elasticity of dimension lumber shapes by a mechanical means consisting of a constant-deflection force measurement of bending forces with a 48-inch bending span. For illustration purposes of this discussion we will describe how the invention relates to the Bechtel et al U.S. Pat. No. 5,503,024 apparatus only, however this method and apparatus may be adapted for use with other kinds of wood testing machines for lumber as well as for panel products.

In machine grading of lumber a series of machine grades are available with the modulus of elasticity property in approximately 5% increments. Grading thresholds must be set with a safety margin above the absolute minimum limit to account for variations in calibration of the equipment and other factors such as the statistical relationship between measured quantities in production equipment and measured quantities in laboratory quality control equipment. Any change that results in a more stable calibration has direct financial benefits by reducing the safety margin requirement.

DEFINITIONS

E—Modulus of elasticity, typically expressed in units of pounds per square inch or gigapascals. This material property expresses the value of "stiffness" that is independent of shape.

I—Moment of inertia, typically expressed in units of inches$^4$. For a rectangular cross section this is equal to $bh^3/12$.

CLT—Continuous Lumber Tester, U.S. Pat. No. 3,196,672.

HCLT—High Capacity Lumber Tester, U.S. Pat. No. 5,503,024

Dimension lumber—structural lumber shapes typically 1½" thick by widths from 2½ to 11¼" in North America, also referred to as "timbers" in other countries with similar sizes expressed in metric units 35 to 45 mm thick by 70 to 300 mm wide.

BRIEF DESCRIPTION OF THE DRAWINGS

The preferred embodiment of the invention is illustrated in the accompanying drawings, in which:

FIG. 1 illustrates a schematic side view of a system of rollers used in a lumber grading machine and including a short test bar used in calibration of the system.

FIG. 2 illustrates a schematic side view of a system of rollers used in a lumber grading machine and including a long test bar used in calibration of the system.

DETAILED DESCRIPTION OF THE PREFERRED EMBODIMENT

Wood Testing Machine

Figure 3:
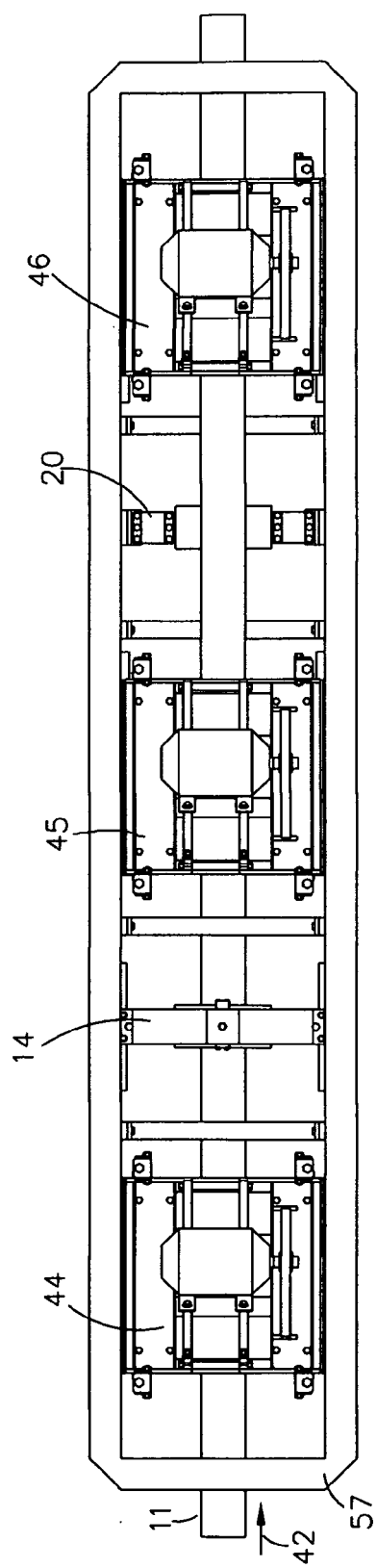
FIG. 3 is a schematic top view of a lumber testing machine.
Figure 4:
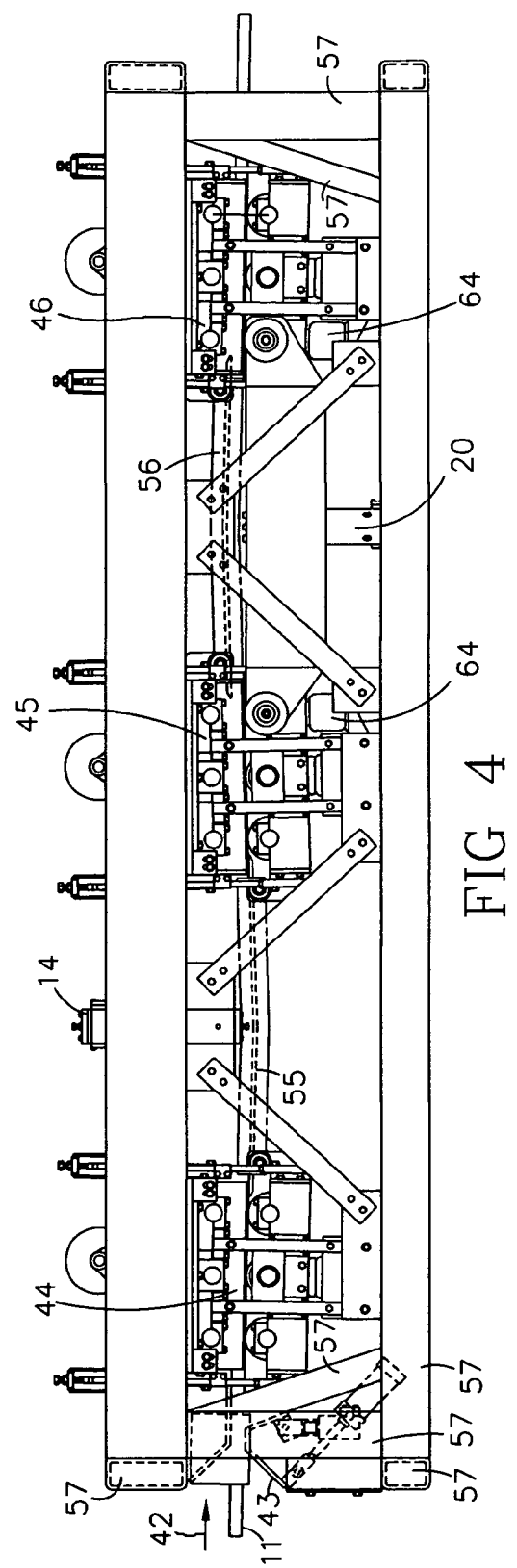
FIG. 4 is a schematic side view of a lumber testing machine.
Figure 5:
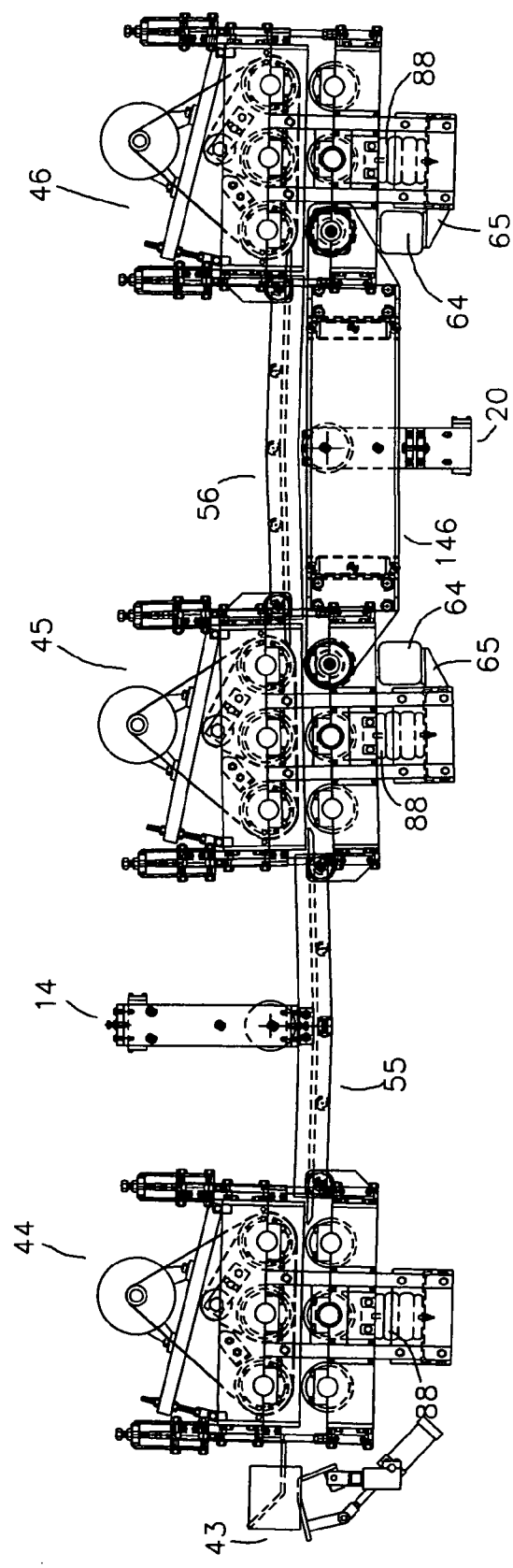
FIG. 5 is a schematic side view of a lumber testing machine with the frame removed to better illustrate the arrangement of components.

The physical arrangement of components for the Bechtel et al apparatus is shown in FIG. 3 and FIG. 4, and internal details are shown in FIG. 5. Two bending spans are connected as shown in FIG. 5, alternately bending the specimen in a downward and an upward direction, or vice-versa. Referring to FIG. 3 and FIG. 4, A load cell connected to a load roller in the load roller assembly 14 measures the bending force as the wood board specimen 11 passes through the machine in a direction 42 and the output of the load cells located in assemblies 14 and 20 are connected to an electronic means for signal processing, detecting features of the bending force signal as the specimen passes through the machine, and then classifying the specimen from the information in the force signal. Clamp roller assemblies 44, 45 and 46 simultaneously grip the wood board specimen from the top and bottom surfaces and urge the movement of the wood board through the machine in the direction 42. The components are placed inside and mounted to frame 57. An in-feed guide 43 assists in directing the leading end of the wood board specimen into the nip of the rollers in the first clamp roller assembly 44. When the leading end of the wood board specimen 11 reaches board guide 55, the leading end comes into contact with board guide 55 and is deflected toward the nip of the first roller pair in clamp roller assembly 45, and thereby brought into contact with the load sensing roller in assembly 14 where the bending force is measured and that information sent along to the electronic means. The process is repeated with the wood board specimen 11 being deflected in the opposite direction by board guide 56 and deflected into contact with the load sensing roller in assembly 20 and into the nip of the first clamp roller in clamp roller assembly 46.

The mechanical means includes two bending sections, one of which is shown schematically in FIGS. 1 and 2, in which a specimen is forced to conform to a path which simulates a simply-supported center-loaded bending span. With the specimen in place in the bending section with span 117 and deflected by a distance 116, the ends of the bending span will be rotated at an angle 118. When the clamp roller group is set at this same angle 118 there is no bending moment introduced at the ends of the bending span and even though the ends of the specimen are "clamped" by the clamp roller group the bending force and deflection relationship is the same as that for a simply-supported center-loaded bending span, if the test bar or lumber specimen is straight. If the lumber specimen is not straight, which is generally the case; the resulting aberrations are compensated by the signal processing means which combines the measurements from the individual oppositely directed bending measurements such that the error arising from bend in the specimen is cancelled. The deflection 116 is defined by the vertical elevation of the load sensing roller 202 and the two rollers 113 located at the span ends and on the same side of the wood board specimen as the load sensing roller 202. FIG. 1 illustrates the arrangement of rollers with a short test bar 12 in place and FIG. 2 illustrates the arrangement of components with a long test bar 13 in place. The deflection 116 is set correctly when the force on the load sensing roller 202 is the same with the long bar 13 in place as it is with the short bar 12 in place.

FEATURES AND ADVANTAGES OF THE PRESENT INVENTION WITH COMPARISON TO THE PRIOR ART

Two types of test bars were formerly used in the calibration process, a long bar and a shorter bar, and later an additional shim part was introduced in an attempt to overcome some of the problems in the calibration of these machines.

Referring to FIG. 1 and FIG. 2, mechanical adjustments are made in a first stage of calibration. The long bar 13 and the short bar 12 are alternately introduced into the bending span and the deflection 116 applied referenced to reference rollers 113 at the load roller 202 is adjusted so the electronic reading for the two test bars is the same, within a measurement tolerance. These measurements and adjustments are repeated with the test bar moved to the two lateral extremes of the lumber guide path as well as with the bars located along the centerline of the lumber path.

Figure 9:
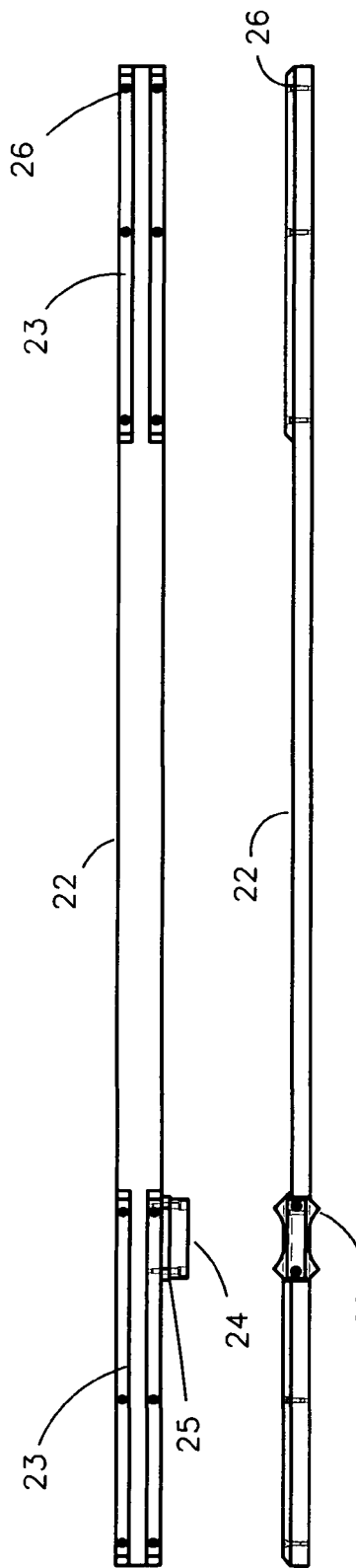
FIG. 9 is a top and side view of a prior art long test bar.

The prior-art long test bar 22 shown in FIG. 9 was constructed of 1"×2½" 2024-T351 aluminum alloy with ⅝" square aluminum "feet" 23 fastened at the ends with recessed socket head cap screws 26 such that the portion engaging the clamp rollers would be at least as thick as the lumber being tested. In a later embodiment a guide 25 was fastened to the side of the bar along with a weight 24 to assist in locating the test bar over one of the rollers in the machine. This guide 25 is manufactured of ½" polyurethane polymer so that it would not damage the rollers or interfere with the measurement. The steel weight 24 helps assure that the guide remains in place while the clamp rollers are closed on the test bar.

The short test bar 27 is manufactured using the same kinds of materials as the long test bar with feet 28 held in place with recessed socket head cap screws 31 and with guide 30 and weight 31 located at the side of the test bar on one end only. This type of test bar has been in use from the time the CLT Continuous Lumber Tester was introduced in about 1962. As can be seen in FIG. 5, when the bars are moved from one bending section to the other, the bar must be rotated 180 degrees about its long axis so the side of the bar opposite the feet 23 and 28 engages the load roller. This is a key distinction from the present invention bars shown in FIG. 6 and FIG. 7 which is designed with top/bottom symmetry so that it may be loaded from either side and is used with the marked side 72 up only. The center mark 74 of FIG. 6 and the center mark 80 of FIG. 7 are cleverly offset from the longitudinal center of the bars 68 and 78 so that the need for an external weight as used in the prior art test bars is eliminated. The guide 70 is fastened to the bar using button head screws 76, making the guide assembly much more compact and less likely to snag on the internal structure of the machine as the bar is being loaded and moved about in the machine during the calibration process. The EI value for each test bar is determined by means of a dead weight tester in which the deflection (strain) is of the bar is determined for an increment of load (stress). The EI value for each test bar of FIG. 6 and FIG. 7 is marked at location 15 on the test bar along with a serial number for the test bar.

Figure 6:
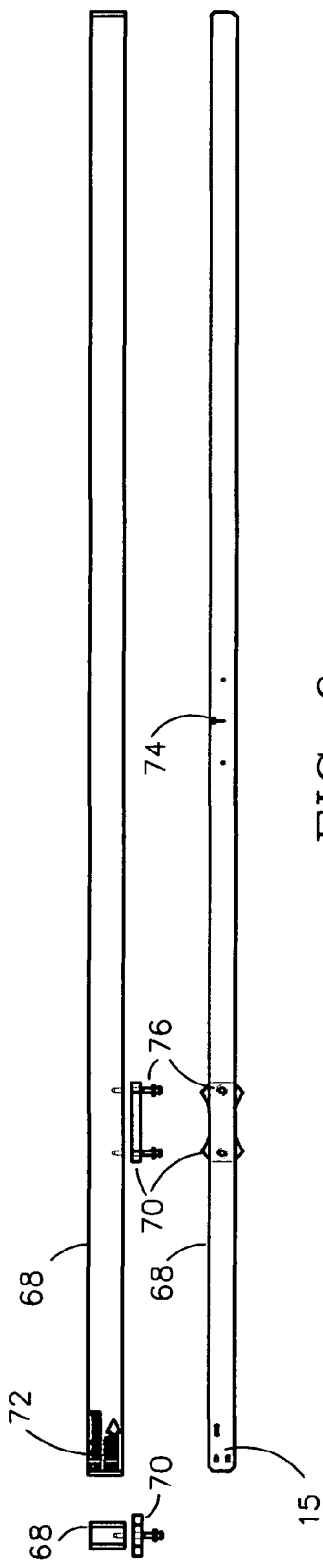
FIG. 6 is a top, end and side view drawing of the improved long test bar used in the present invention.
Figure 7:
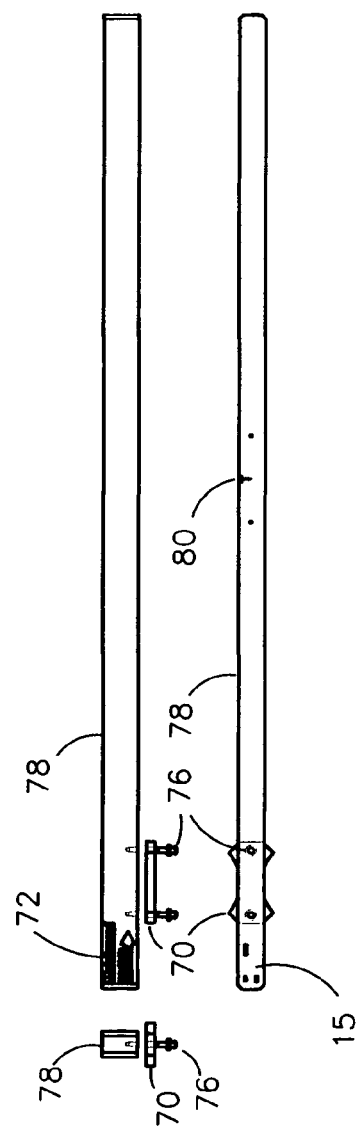
FIG. 7 is a top, end and side view drawing of the improved short test bar used in the present invention.

Referring to FIG. 1, the long bar 13 is 22 of FIG. 9 in the prior art, or 68 of FIG. 6 in the present invention. This long test bar engages all the clamp rollers at the ends of the bending span as well as the load roller as shown in FIG. 1. The short bar 12 engages only the load roller and the two clamp rollers at the ends of the bending span as shown in FIG. 2. This short test bar is 27 of FIG. 10 in the prior art or 78 of FIG. 7 in present invention.

Figure 8:
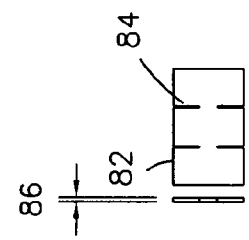
FIG. 8 is a top and side view of a shim used with both the present invention and prior art methods.

In the next stage of calibration it is desired that the relationship between force and voltage output of the load cells in the two bending sections match within a tolerance. In an earlier prior art method this was accomplished using only the short test bar, and adjustments were made in the electronic gain of the load cell calibration circuitry so that equal readings were observed for the short bar in the two bending sections. This was later refined to include adjustment against a reading with and without a shim 82 of FIG. 8 between the short test bar and the load roller. This shim has a thickness 86 of approximately 0.200", and is designed to increment the deflection by its thickness without interfering with the curvature of the test bar in the vicinity of the load roller. This is accomplished by fine cuts 84 in the shim arranged to reduce the cross section near the line of contact with the load roller, thus increasing the bending compliance of the shim so that it will conform to the bending curvature of the test bar when in place and loaded. This shim 82 is used in later prior art methods as well as in the present method.

In the third stage of calibration by the prior art method, the long test bar readings are recorded. Then a sample of lumber is run through the machine and readings recorded. Then the lumber sample is measured for modulus of elasticity (E) on laboratory equipment. The readings from the machine and from the lab equipment are then compared. If the coefficient of determination is less than 0.95 the measurements are repeated. An adjustment factor is calculated from the regression line between the production equipment and the lab equipment readings and a gain adjustment is calculated which will adjust the machine readings to match at an E value of 1.8 million PSI. This adjustment factor is then applied by calculating new long bar values for the machine for the two bending sections, inserting the long test bar in to each of the bending sections of the machine and adjusting the electronic gain to the new calculated long test bar values.

Typically the third stage of calibration is done only occasionally and the long test bar values from the last run of this calibration process are used in subsequent daily calibrations.

Both the Keller and Bechtel apparatus used the same calibration procedure when they were introduced and both procedures suffered from the shortcomings of that calibration procedure. With the machine idle, an aluminum test bar is introduced into a first bending section of the machine and the electronic means is adjusted for the desired output with the test bar in place, then that test bar is moved to a second loading section, rotated about the long axis by 180 degrees so load is applied to the same side of the bar and the second load cell amplifier is adjusted for its desired output, that desired output being the same for both bending sections with a value specific to the properties of the test bar.

This prior art calibration procedure works fine as long as the machine is adjusted mechanically to precisely equal bending deflections and those deflections never change during operation of the equipment and there is no change in the shape of the test bar. A calibration problem arises when a deflection change is introduced into the bending apparatus, resulting in a shift in calibration even though the load force was adjusted to precisely the correct value with the test bar in place. A problem of a slightly different type is introduced if the test bar is not exactly straight along its long axis, or if that straightness changes over time.

Figure 11:
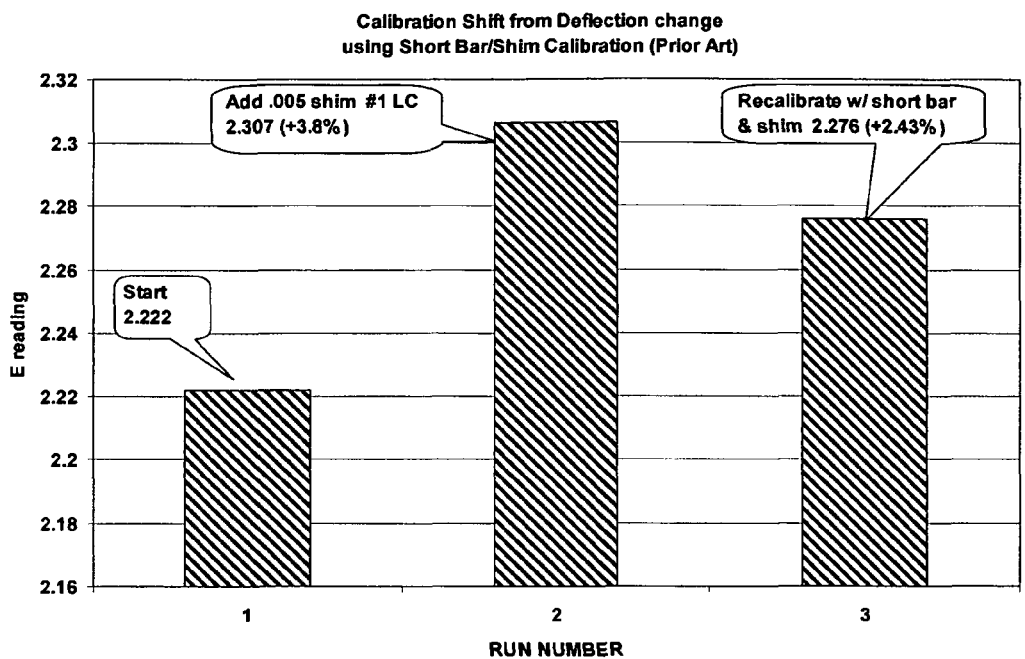
FIG. 11 is a bar graph showing calibration error arising from a change in deflection in prior art method.

The original design of the test bars was carried through from the first Keller CLT [1] and has been in use from about 1962 to 2007. Un-explained calibration shifts were observed in a number of instances without a satisfactory explanation. Further investigation was launched to determine the cause and eliminate the effects. An experiment was devised to determine the magnitude of a calibration shift in the presence of a change in deflection in the machine. Readings were taken on a sample of lumber, a known deflection change was introduced into one of the bending sections by means of a 0.005" thick shim placed under the load cell in a way that would increase the deflection in one bending section by the shim thickness and the readings were then repeated. Then the machine was recalibrated using the prior art methods and apparatus, and the lumber sample was again run to see if the change in calibration was properly compensated in the calibration process. The graph in FIG. 11 shows the results. This compares the average values for the lumber sample before and after the deflection change (run 1 and 2) and the values after the recalibration (run 3).

FIG. 11 shows the readings increased after the 0.005" shim was added to the deflection in one of the bending sections by 3.8%. After recalibrating with the deflection offset shim in place the readings were still 2.43% above their initial values. If a deflection change is made within the tolerance allowed for deflection change we find that the calibration of the equipment would change by more than 5%, which is a full grade level in production of MSR lumber. This shift is seen to be an unacceptable one, and one that is not indicated to the operator in any way except a change in the properties of the graded material.

Another problem with the previous method is that it is impossible to manufacture the test bars sufficiently straight so that equal results can be obtained from two different sets of test bars. This makes particularly difficult calibrating two machines (with different sets of test bars) so they read the same. Fleet calibration, adjusting two or more machines to the same calibration, is approximate at best.

Another problem with the previous method is that when you compare the machine readings with the laboratory readings on a different sample of lumber, you get a different calibration point. This arises because the distribution of E values is different between lumber samples and slight non-linear effects in the measurement process cause the calibration point to shift. Thus calibration is against a moving target, not a desirable situation.

After much experimental work it was determined that in fact the unexplained calibration shift could be traced directly to a deflection change. In the calibration of any measurement system there must be a specified tolerance for every adjustment, particularly in the age of the computer in which if you set the tolerance level to zero on a measurement you will always get an out-of-tolerance failure indicated. It was determined during these experiments that the practical tolerance limit on adjustment of the deflection in the machine would take the calibration error outside an acceptable tolerance range because the procedure using the original test bar design did not fully compensate for the deflection change.

Experience over the years has shows that sometimes test bars become damaged and bent, and that whenever this happens there is a shift in machine calibration with no indication to the operator that this has taken place. It only shows up in reduction of grade yield or out-of-control situations in the quality control testing procedures, either of which is time-consuming and expensive to correct.

It may be useful to point out that the prior art calibration system had been in use for a period of about 45 years in up to 120 plant locations in 10 different countries, and at no time during that period of exposure to operators did anyone discover the cause of the unexplained calibration shifts that occurred on a fairly regular basis.

THE PRESENT INVENTION

The apparatus of the present invention provides for test bars that can be loaded from either side so that they may be used same-side-up in the machine. The mechanical features of the test bars are simplified eliminating many parts, and the elimination of the side weight used in the prior art bars makes the bars more streamlined and easier to load into the machine and move about during the calibration process.

What the New Process does
1. New calibration process takes into full account any changes in machine deflection plus any bend in the test bars to provide for absolute calibration of the equipment.
2. If there is a deflection change in one of the bending sections the calibration process of the present invention computes new gain settings to be used in both bending sections to return the system to correct calibration.
3. The software includes color-coded sequencing to take the operator through all steps necessary to calibrate the equipment, and acts as a built-in checklist with tolerance and error checking.
4. The software allows each mill to set on-screen reminders for needed calibration intervals.
5. The software provides for printing calibration records directly from the system.
6. The software displays previous calibration values for easy reference.
7. The software maintains a procedure log of calibration.
8. The new calibration bars of the present invention remain same side up for both bending sections.
9. The new process replaces all previous calibration equipment and processes for this system.

The present invention solves the problems of the prior art by taking the calibration through a new set of steps. A different type of test bar is required to carry out these steps.

1. The first steps of making mechanical adjustments of deflection are the same as for prior art methods.
2. In the second step each bending section of the machine is adjusted in gain so that the relationship between force and indicated output is the same for both bending sections.

This step is accomplished by first inserting a short test bar, placing it under load and recording a beginning measurement value of bending force. The short test bar engages only the rollers at the ends of the bending span and the load roller. Then the load is removed and a shim is placed between the test bar and the load roller in the bending span and the load is reapplied. A second measurement value of bending force is recorded. The difference between the first and second force value measurements gives the relationship between force and electronic output. These results are used in Step 3 of the present invention.

3. In the third step a long test bar is introduced of a new symmetric design that can be loaded from either side. It stays same-side-up throughout the calibration process. It is first placed in the machine with a marked top face "up" in the first bending section, the load is applied and a measurement is taken of the electronic representation of the applied force.

The test bar is then moved to the second bending section with the same top face up, and it is loaded in the opposite direction and the electronic representation of the applied force is recorded.

At this point we have six measurements. The difference between the short test bar readings with and without the shim is determined for both bending sections. After adjustment these two values will be equal.

In the next step we will adjust the two load cell amplifiers (or digital gain multipliers) such that the average of the two long bar values is equal to a desired calibration value, while at the same time making the two short-bar-shim values equal.

4. An adjustment factor is calculated based ratio of the two short bar differences. This number is combined with the average of the two long bar values to determine an adjustment factor for each load cell amplifier. This adjustment factor is introduced into the load cell amplifier gains or digital gain multipliers.

Upon completion of these steps we have calibrated the machine against the long test bar stiffness, which has been previously measured and recorded. The effect of any bend in the long test bar has been compensated by bending in two directions.

This procedure compensates for mechanical discrepancies in the equipment and makes possible more stable operation, and thereby reducing the coefficient of variation of the calibration point. When this is accomplished one can reduce the grade threshold values which had previously been set with a margin of safety to accommodate the variation of calibration which this new apparatus and procedure now eliminates. The result is more accurate grading and higher grade yields and profits from a given lumber supply.

Figure 12:
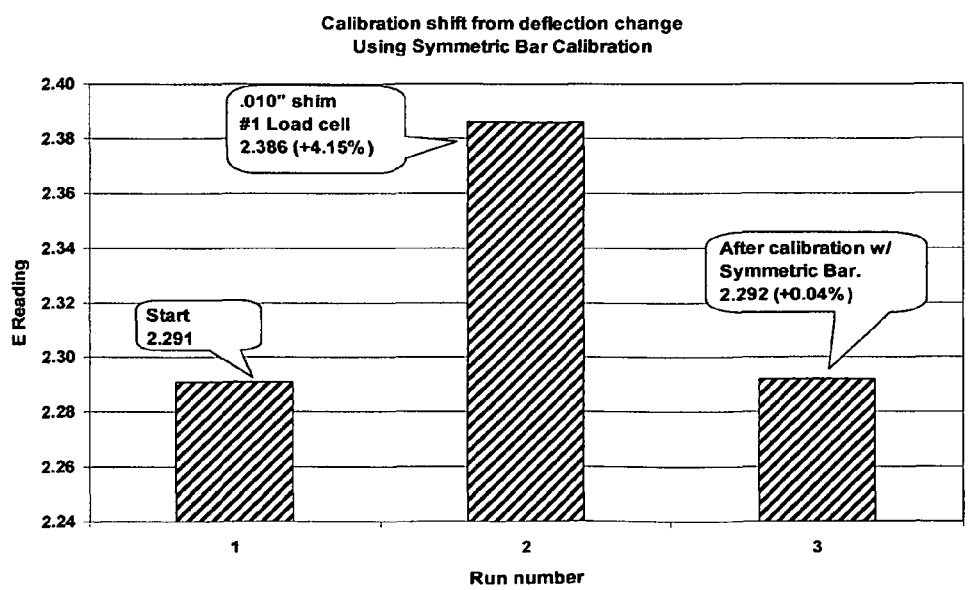
FIG. 12 is a bar graph showing how calibration error arising from a deflection change is eliminated in the present invention.

Performance of the new symmetric bar calibration system of the present invention is illustrated in FIG. 12. In the FIG. 12 we see the results of repeating the calibration shift experiment, this time with a shim displacement of 0.010", twice the value seen in the previous experiment described above, but this time with the equipment recalibrated after Run 2 using the method and apparatus of the present invention. We see that the calibration shift in Run 2 compared with Run 1 was 4.15% and after recalibration with the improved method of the present invention the calibration shift was reduced to 0.04%, which for all practical purposes is a negligible error.

The steps of this procedure are embodied in a computer program that directs the operator through the several steps of the process, checks for errors at each stage and records the results in a calibration log for future reference.

An advantage of this method and apparatus is that the calibration results are now directly dependent upon only the EI value of the test bar, which EI value can be measured and recorded, and it becomes very simple and direct to include the EI measurement in the computer computations so that new test bars may be installed without making any other adjustments in the equipment.

Another advantage of this method and apparatus is that the calibration is independent upon the machine deflection settings and independent of the test bar straightness, even if the bar straightness changes over time.

Another advantage of the present method is that fleet calibration can be done very accurately because the bend in the test bars is no longer a factor in calibration and the EI value of the test bar is included in the calculation. This means that a number of machines can be calibrated to match their readings, a difficult process with the prior art methods.

The calibration resulting from this method and apparatus remains dependent upon the temperature effects on the EI product for the test bar. The effects of this dependency can be minimized by maintaining the test bars at a controlled temperature, or by applying a small adjustment factor to take into account the temperature effects.

Figure 10:
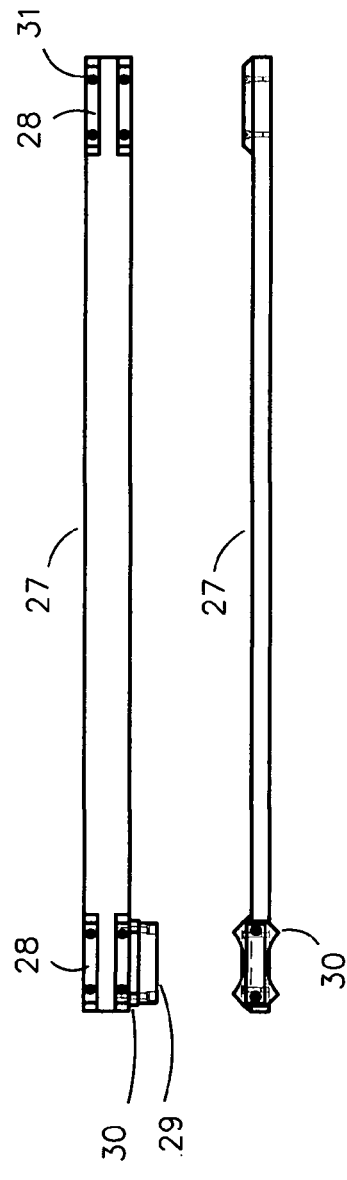
FIG. 10 is a top and side view of a prior art short test bar.

It should be pointed out here also that while the short test bar 78 of FIG. 7 is functionally symmetric so that it may be loaded from either side, that the short test bar of the prior art 27 of FIG. 10 may be used in the present invention because it is not necessary to load the short test bar from either side to set the load cell conversion gains equal. The short test bar is replaced in new manufacture with test bar 78 of FIG. 7 because it is simpler and more streamlined and easier to handle during calibration. Also it is convenient to make the short bar and shim measurements using the same scale setting in the data processing means as is used with the long test bar, so the short test bar and the long test bar are constructed of the same materials in the preferred embodiment.

Method.

To reiterate, the method consists of the following steps:

1. Set conversion gain (volts per pound of force) equal in two bending measurement sections. (G1=G2)
2. Set k(G1+G2)/2 so that 1 volt (or the number 1.00) represents 1.00 million PSI in the test specimen.
3. Use of test bar that does not change orientation between two bending test sections so that effect of bend in the test bar is cancelled.

Apparatus.

1. Test bars are symmetric design so they may be loaded from either side.
2. Long test bar engages all the rollers in restraint roll section and loading roller.
3. Short test bar that engages only loading roller and two end-span rollers.
4. Shim to be used with sort test bar to establish G1=G2.
5. Computer software to manage calibration sequence and log results In compliance with the statute, the invention has been described in language more or less specific as to structural features. It is to be understood, however, that the invention is not limited to the specified features shown, because the means and construction herein disclosed comprise a preferred form of putting the invention into effect. The invention is, therefore, claimed in any of its forms or modifications within the proper scope of the appended claims appropriately interpreted in accordance with the doctrine of equivalents.

The invention claimed is:

1. An apparatus for calibrating a wood testing machine with a first bending section means and a second bending section means each with a bending span defined by two end-span rollers, one in each of two clamp roller groups and a load sensing roller located at or about a center of the bending span with a force measurement means that produces output values proportional to a force applied by the load sensing roller when said roller bends elongate material by a predetermined deflection whereby the predetermined deflection in the first bending section means is a first predetermined deflection and the predetermined deflection in the second bending section means is a second predetermined deflection and the first predetermined deflection is in a direction substantially opposite to the second predetermined deflection, comprising:
   a. A test bar that can be positioned within either the first or second bending section means such that the test bar will bend in one direction in one bending span and in an opposite direction in the other bending span such that a first test bar reading and a second test bar reading are produced equal to output values from a first and second force measurement means, respectively, said test bar having an EI value equal to a product of a modulus of elasticity (E) of a test bar material and a moment of inertia (I) for a cross section of the test bar, and;
   b. a calibration shim of predetermined thickness that can be introduced between a load sensing roller and the test bar when the test bar is bent in the first bending section means or the second bending section means, such that a shim reading equal to a change in output value is produced for each bending section means with said readings proportional to the thickness of the calibration shim and the EI value of the test bar whereby a first shim reading is produced for the first bending section means and a second shim reading is produced for the second bending section means, and;
   c. a first calculating means that determines a shim scale factor for each bending section means such that a product of the first shim scale factor and the first shim reading equals a product of the second shim scale factor and the second shim reading, and;
   d. a second calculating means that determines an overall scale factor such that a sum of the product of the first shim scale factor and the first test bar reading and the product of the second shim scale factor and the second test bar reading, multiplied by the overall scale factor is at a predetermined relationship to the EI value of the test bar,
   whereby the first shim scale factor, the second shim scale factor and the overall scale factor together are the calibration of the wood testing machine.

2. The apparatus of claim 1 further comprising a signal processing means that uses the first shim scale factor, the second shim scale factor and the overall scale factor to produce calibrated wood testing machine output values for wood that are equal to the sum of the product of the first shim scale factor and a first force measurement output value for wood in the first bending section means and the product of the second shim scale factor and a second force measurement output value for the wood in the second bending section means, multiplied by the overall scale factor with said calibrated wood testing machine output value at a predetermined relationship to a modulus of elasticity of the wood.

3. The apparatus of claim 1 wherein the test bar used to produce the shim readings and determine the shim scale factors is a short test bar that engages only the load sensing roller and the two end-span rollers and the test bar used to produce the test bar readings and determine the overall scale factor is a longer test bar that engages all clamping rollers in each of the clamp roller groups and the load sensing roller.

4. The apparatus of claim 1 wherein the second calculating means includes in input for EI product of a test bar whereby a plurality of test bars may be used conveniently while maintaining the calibration of the wood testing machine for all test bars.

5. The apparatus of claim 1 further comprising a test bar made of aluminum with a guide attached to aid in placement in the wood testing machine.

6. The apparatus of claim 1 wherein the test bar is not perfectly straight relative to its longest axis.

7. The apparatus of claim 1 wherein the test bar has an EI value that is within a range of a product of moment of inertia and modulus of elasticity of wood to be tested.

8. The apparatus of claim 1 wherein the first predetermined deflection and the second predetermined deflection are not equal.

9. The apparatus of claim 1 wherein the test bar is arranged with a guide whereby the test bar can be placed in the wood testing machine with a center of a long axis of the test bar offset from the load sensing roller such that one end of the test bar will rest on an end-span roller with the guide piece in contact with said end-span roller such that the bar will be held in place under its own weight prior to being deflected, thereby making possible calibration when the wood testing machine is installed at an angle to the horizontal.

10. The apparatus of claim 1 further comprising a computer software system that provides the first calculating means and the second calculating means and directs an operator through a sequence of calibration steps whereby calibration may be accomplished in an orderly and logical manner.

11. The computer software system of claim 10 further comprising the function of recording and producing a log of activity and results during the calibration.

12. A method for calibrating a wood testing machine with a first and a second bending section means each with a bending span defined by two end-span rollers, one in each of two clamp roller groups and a load sensing roller located at or about a center of the bending span with a force measurement means that produces output values proportional to a force applied by the load sensing roller when said roller bends elongate material by a predetermined deflection whereby the predetermined deflection in the first bending section means is a first predetermined deflection and the predetermined deflection in the second bending section means is a second predetermined deflection and the first predetermined deflection is in a direction substantially opposite to the second predetermined deflection, comprising the steps of:
   a. positioning a test bar within both the first and second bending section means such that the test bar will bend in one direction in one bending span and in an opposite direction in the other bending span such that a first test bar reading and a second test bar reading are produced equal to output values from a first and second force measurement means, respectively, said test bar having an EI value equal to a product of a modulus of elasticity (E) of a test bar material and a moment of inertia (I) for a cross section of the test bar, and;

b. introducing a calibration shim of predetermined thickness between the load sensing roller and the test bar when the test bar is bent in a first bending section or a second bending section, such that a shim reading equal to a change in output value is produced for each bending section means with said readings proportional to the thickness of the calibration shim and the EI value of the test bar whereby a first shim reading is produced for the first bending section and a second shim reading is produced for the second bending section, and;

c. calculating by a first calculating means a shim scale factor for each bending section means such that a product of the first shim scale factor and the first shim reading equals a product of the second shim scale factor and the second shim reading, and;

d. calculating by a second calculating means an overall scale factor such that a sum of the product of the first shim scale factor and the first test bar reading and the product of the second shim scale factor and the second test bar reading, multiplied by the overall scale factor is at a predetermined relationship to the EI value of the test bar, whereby the first shim scale factor, the second shim scale factor and the overall scale factor together are the calibration of the wood testing machine.

13. The method of claim 12 wherein the first shim scale factor, the second scale factor and the overall scale factor are used to process the output values from the first and second force measurement means to determine values that are at a predetermined relationship to a modulus of elasticity of the wood measured by the wood testing machine.

14. The method of claim 12 wherein the steps of determining the change in output values and determining the test bar readings are performed in any sequence.

15. The method of claim 12 wherein the first shim scale factor, the second shim scale factor and the overall scale factor are applied as digital gain multipliers in a digital signal processing means.

16. The method of claim 12 wherein the first shim scale factor, the second shim scale factor and the overall scale factor are applied as amplifier gains in an analog signal processing means.

17. The method of claim 12 further comprising the step of first measuring the EI product for said test bar, and entering said EI product into said second calculating means whereby a replacement test bar may be introduced by simply measuring a replacement EI product for the replacement test bar and entering the replacement EI product in the second calculating means.

18. A method for calibrating a wood testing machine with a first and a second bending section means each with a bending span defined by two end-span rollers, one in each of two clamp roller groups and a load sensing roller located at or about the center of the bending span with a force measurement means, said force measurement means including a force transducer means and a load cell amplifier means with a load cell amplifier gain, that produce output values proportional to the force applied by the load sensing roller when said roller bends elongate material by a predetermined deflection whereby the predetermined deflection in the first bending section means is a first predetermined deflection and the predetermined deflection in the second bending section means is a second predetermined deflection and the first predetermined deflection is in a direction substantially opposite to the second predetermined deflection, comprising the steps of:

a. setting equal the product of a first predetermined sensitivity of a first force transducer means and a first load cell amplifier gain for the first bending section and the product of a second predetermined sensitivity of the second force transducer means and a second load cell amplifier gain for the second bending section, and;

b. positioning a test bar within both the first and second bending section means such that the test bar will bend in one direction in one bending span and in the opposite direction in the other bending span such that a first test bar reading and a second test bar reading are produced equal to output values from the first and second force measurement means, respectively, said test bar having an EI value equal to a product of a modulus of elasticity (E) of a test bar material and a moment of inertia (I) for a cross section of the test bar, and;

c. calculating by a second calculating means an overall scale factor such that a sum of the first test bar reading and the second test bar reading, multiplied by the overall scale factor is at a predetermined relationship to the EI value of the test bar, whereby the product of predetermined sensitivity of force transducer means, load cell amplifier gain and the overall scale factor together are the calibration of the wood testing machine.

19. The method of claim 18 further comprising the step of first measuring the EI product for said test bar, and entering said EI product into said second calculating means whereby a replacement test bar may be introduced by simply measuring a replacement EI product for the replacement test bar and entering the replacement EI product in the second calculating means.

20. The method of claim 18 wherein the overall scale factor is used to process the output values from the first and second force measurement means to determine values that are at a predetermined relationship to the modulus of elasticity of wood measured by the wood testing machine.

* * * * *